(12) United States Patent
Mirzaei et al.

(10) Patent No.: US 11,818,827 B2
(45) Date of Patent: Nov. 14, 2023

(54) METHODS AND SYSTEMS FOR POWER SUPPLY

(71) Applicant: GE Precision Healthcare LLC, Wauwatosa, WI (US)

(72) Inventors: Saeid Mirzaei, Muskego, WI (US); Eric Aasen, Pewaukee, WI (US); Todd Filtz, Hartland, WI (US); Anand Amirtharaj Arokiaswamy, Pewaukee, WI (US)

(73) Assignee: GE Precision Healthcare LLC, Wauwatosa, WI (US)

( * ) Notice: Subject to any disclaimer, the term of this patent is extended or adjusted under 35 U.S.C. 154(b) by 54 days.

(21) Appl. No.: 17/341,259

(22) Filed: Jun. 7, 2021

(65) Prior Publication Data

US 2022/0394837 A1 Dec. 8, 2022

(51) Int. Cl.
*H02J 9/06* (2006.01)
*H05G 1/12* (2006.01)
*H05G 1/14* (2006.01)

(52) U.S. Cl.
CPC ............. *H05G 1/12* (2013.01); *H02J 9/061* (2013.01); *H05G 1/14* (2013.01)

(58) Field of Classification Search
CPC .......... A61B 6/032; A61B 6/4435; A61B 6/56
USPC ......................................................... 307/22
See application file for complete search history.

(56) References Cited

U.S. PATENT DOCUMENTS

| | | | |
|---|---|---|---|
| 5,483,570 A | 1/1996 | Renshaw et al. | |
| 5,995,584 A | 11/1999 | Bhatt | |
| 6,327,340 B1 | 12/2001 | Runnoe | |
| 6,891,928 B2 | 5/2005 | Martin et al. | |
| 7,050,541 B2 | 5/2006 | Bittl | |
| 2005/0278075 A1* | 12/2005 | Rasmussen | H02J 9/06 700/286 |
| 2007/0009095 A1 | 1/2007 | Turaga et al. | |
| 2009/0116618 A1* | 5/2009 | Nakayama | H05G 1/10 378/107 |
| 2009/0179496 A1* | 7/2009 | Ho | H02J 9/062 307/66 |
| 2017/0085122 A1* | 3/2017 | Nasiri | A61B 6/56 |
| 2018/0263591 A1* | 9/2018 | Shanthakumar | H02J 3/32 |

FOREIGN PATENT DOCUMENTS

WO WO2021/247278 * 12/2021

* cited by examiner

*Primary Examiner* — Rexford N Barnie
*Assistant Examiner* — Xuan Ly
(74) *Attorney, Agent, or Firm* — McCoy Russell LLP

(57) ABSTRACT

Various systems are provided for a power supply system. In one example, the system includes a power distribution unit configured to receive power from a main power source and an uninterruptible power supply (UPS), wherein the UPS is configured to directly power an output AC load, the UPS is further configured to power an output DC load after coupled through one or more transformers.

11 Claims, 7 Drawing Sheets

METHODS AND SYSTEMS FOR POWER SUPPLY

TECHNICAL FIELD

Embodiments of the subject matter disclosed herein relate to providing power to medical imaging system in response to a main power source being absent due to a utility power outage.

BACKGROUND

A computerized tomography (CT) imaging system may receive power from a main power supply, such as a utility power source. The utility power source may be connected to a utility grid. During some conditions, the main power supply may not be provided in response to power outages, component failures or due to the main power supply being unexpectedly cut-off.

Certain components within a CT imaging system, such as an x-ray source may need to cool down during a shutdown before the main power supply is turned off from the imaging system. Unexpected power outages may damage certain components, such as an x-ray source in the CT imaging system. To protect these components and extend their life, it may be desired to provide back-up power during unexpected power outages of the main power supply in order to maintain a cool down routine of the components even when the main power supply is not available.

SUMMARY

This summary introduces concepts that are described in more detail in the detailed description. It should not be used to identify essential features of the claimed subject matter, nor limit the scope of the claimed subject matter.

In one aspect, a system comprises a power distribution unit (PDU) configured to receive power from a main power source and an uninterruptible power supply (UPS), wherein the UPS is configured to directly power an output AC load, the UPS is further configured to power an output DC load after coupled through one or more transformers.

In another aspect, a medical imaging system, comprises a gantry coupled to an output DC load, a power cabinet coupled to an output AC load, a power distribution unit (PDU) comprising a primary transformer, a first secondary transformer, and a second secondary transformer, wherein the power distribution unit is configured to receive power from one of a main power source and an uninterruptible power supply (UPS); and a controller with computer readable instructions stored on memory thereof that cause the controller to adjust a position of an input power switch and a forward switch to an open position in response to power from the main power source being unavailable; and adjust a position of a switch to couple power form the UPS to the output AC load and the output DC load.

In yet another aspect, A method for a computer-tomography (CT) system, the method executed via instructions stored on memory of a controller, the method, comprising in response to a main power source being unavailable; powering an output AC load directly via an uninterruptible power supply (UPS); powering an output DC load via power from the UPS to a second secondary transformer, to a primary transformer, to a first secondary transformer, and through a rectifier.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
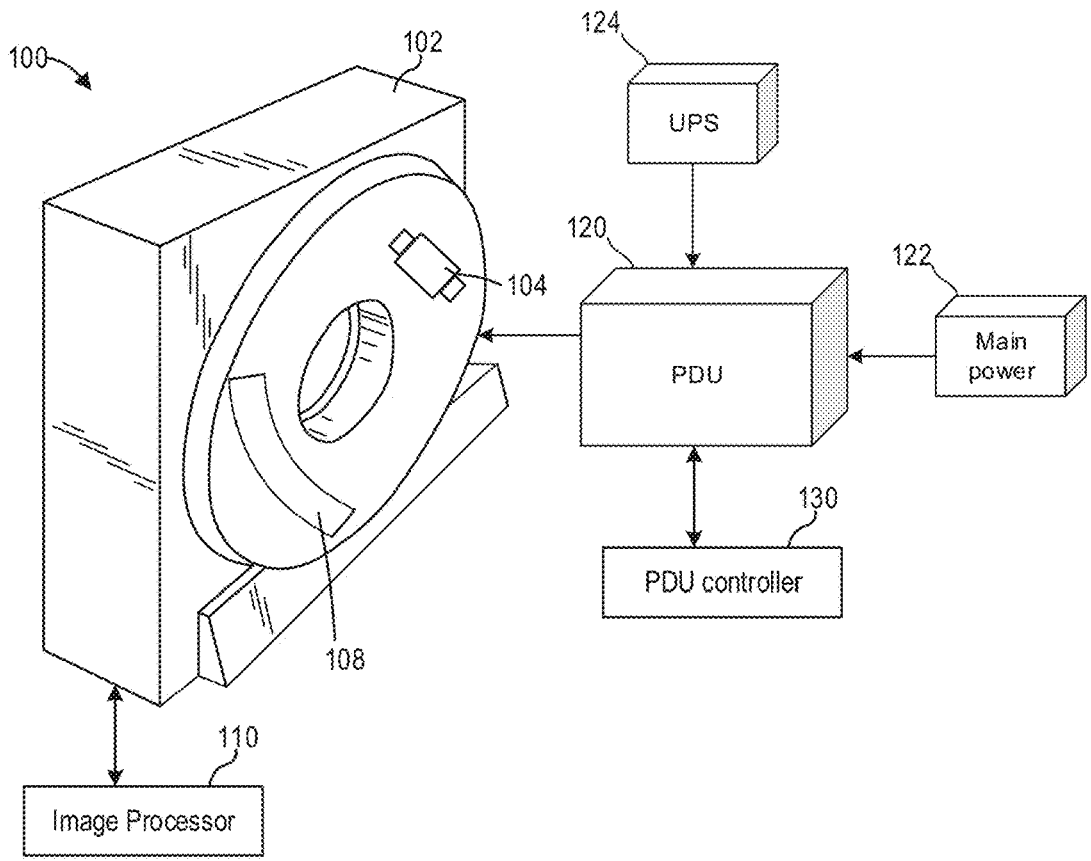
FIG. 1 shows a pictorial view of an imaging system, according to an embodiment.
Figure 2:
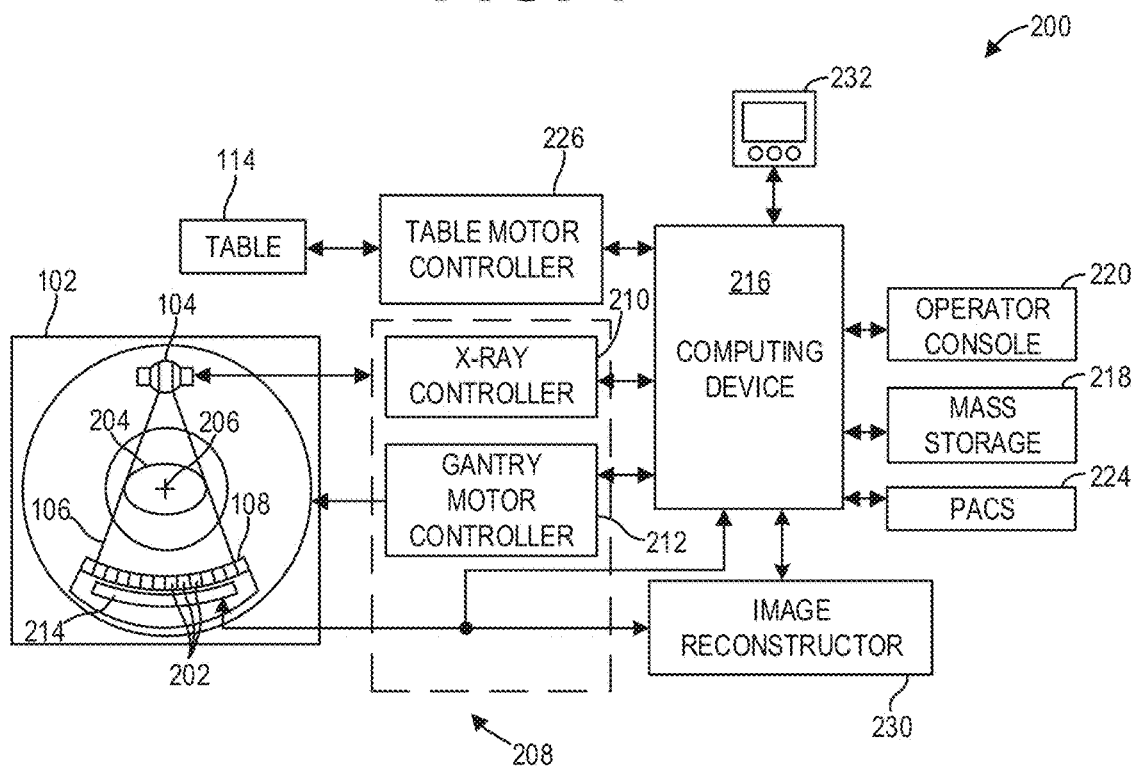
FIG. 2 shows a block schematic diagram of an exemplary imaging system, according to an embodiment.
Figure 3:
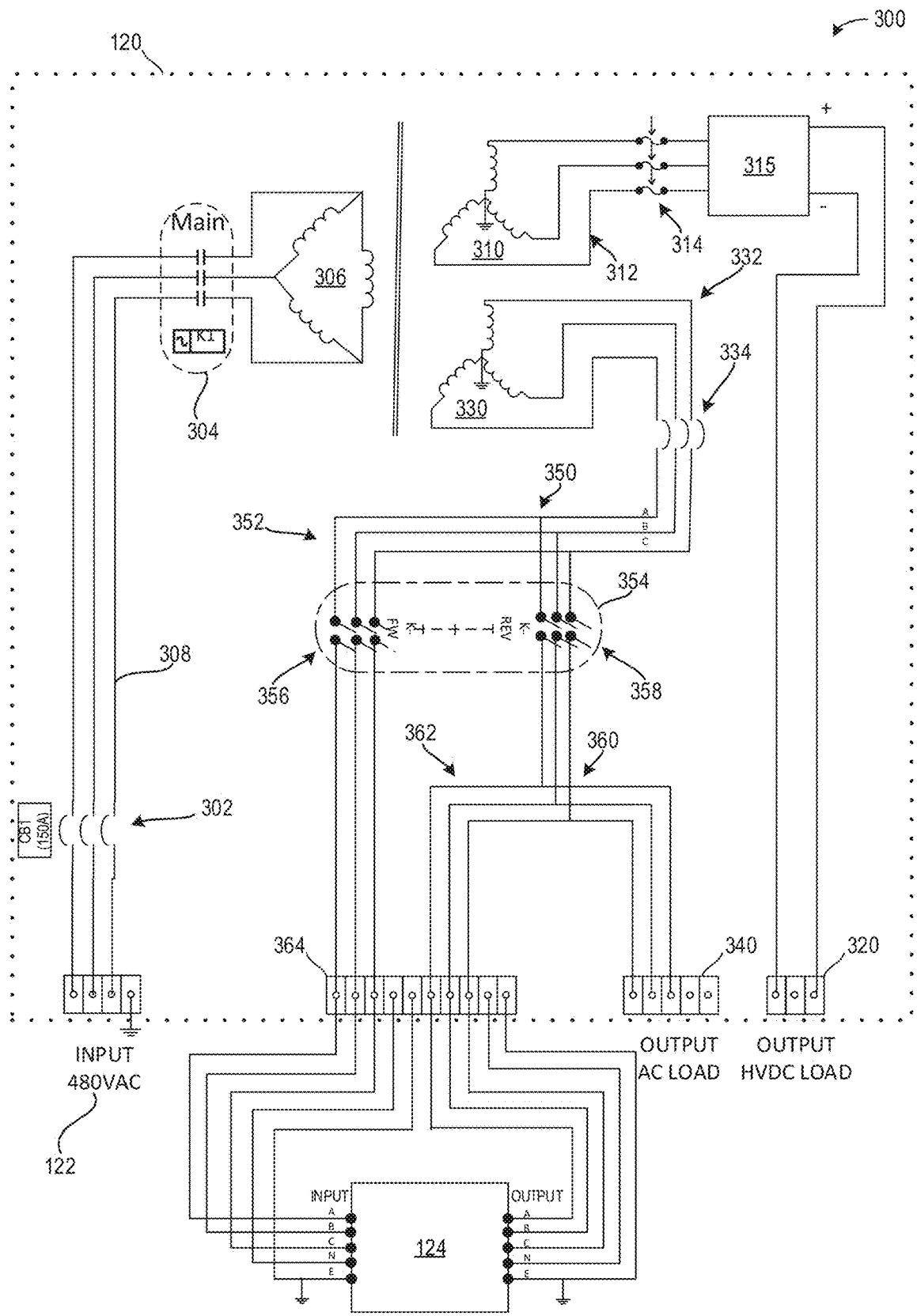
FIG. 3 shows a detailed illustration of an electrical circuitry coupling between a main power supply and an uninterruptible power supply (UPS) to a power distribution unit (PDU).
Figure 4:
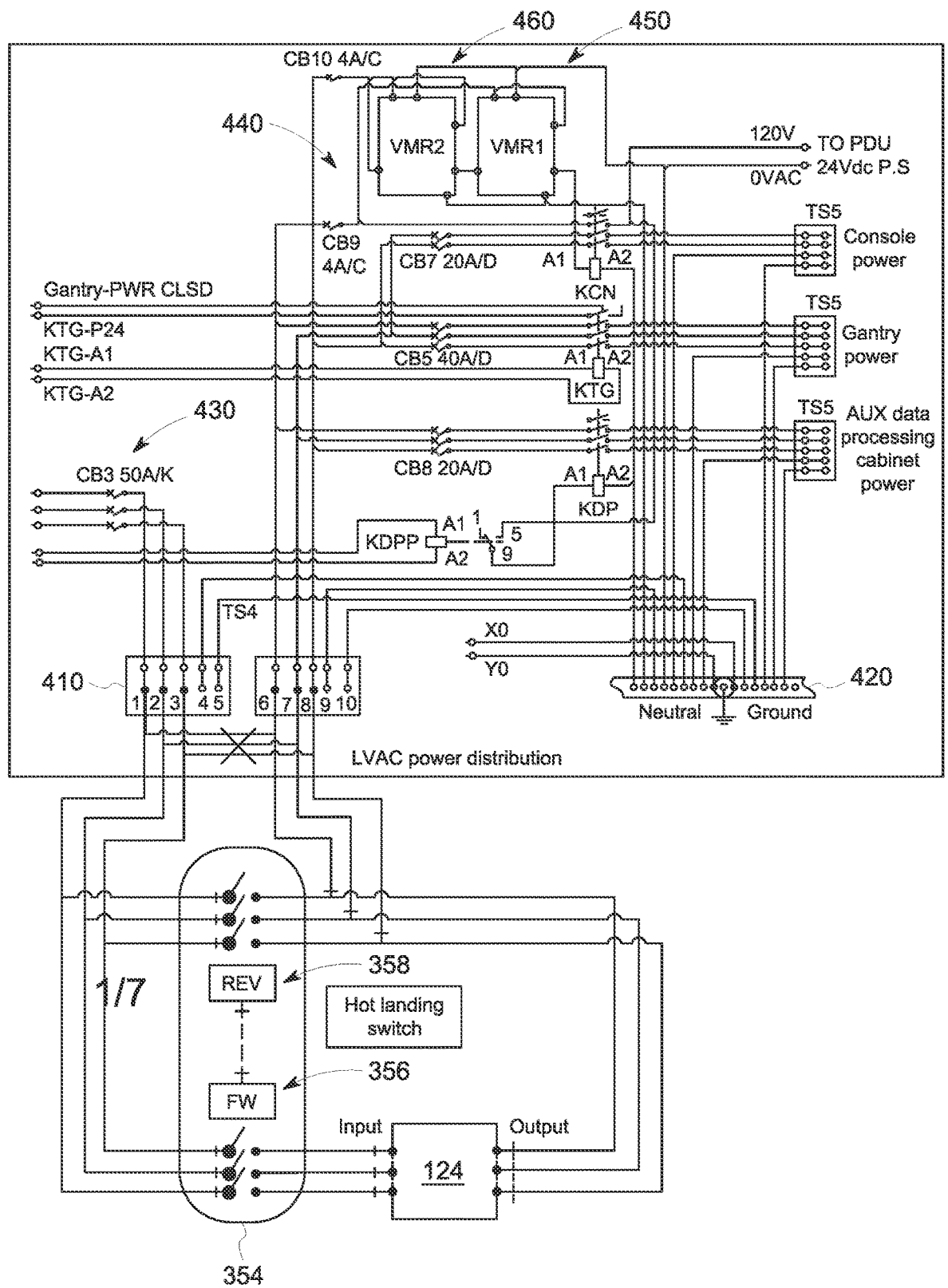
FIG. 4 shows a detailed illustration of the UPS coupled to the PDU.
Figure 5:
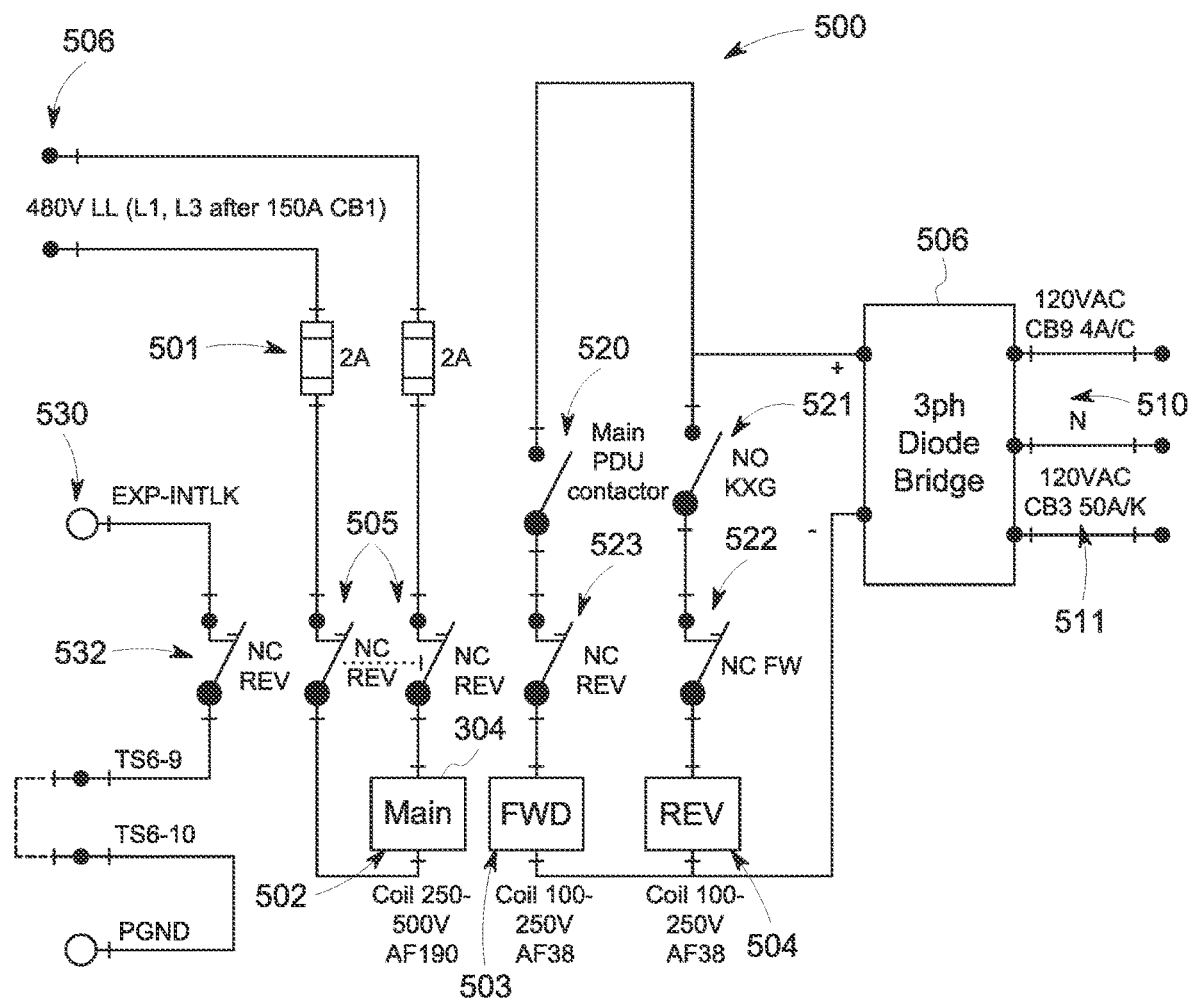
FIG. 5 shows a control circuit of a hot landing switch of the UPS.
Figure 6:
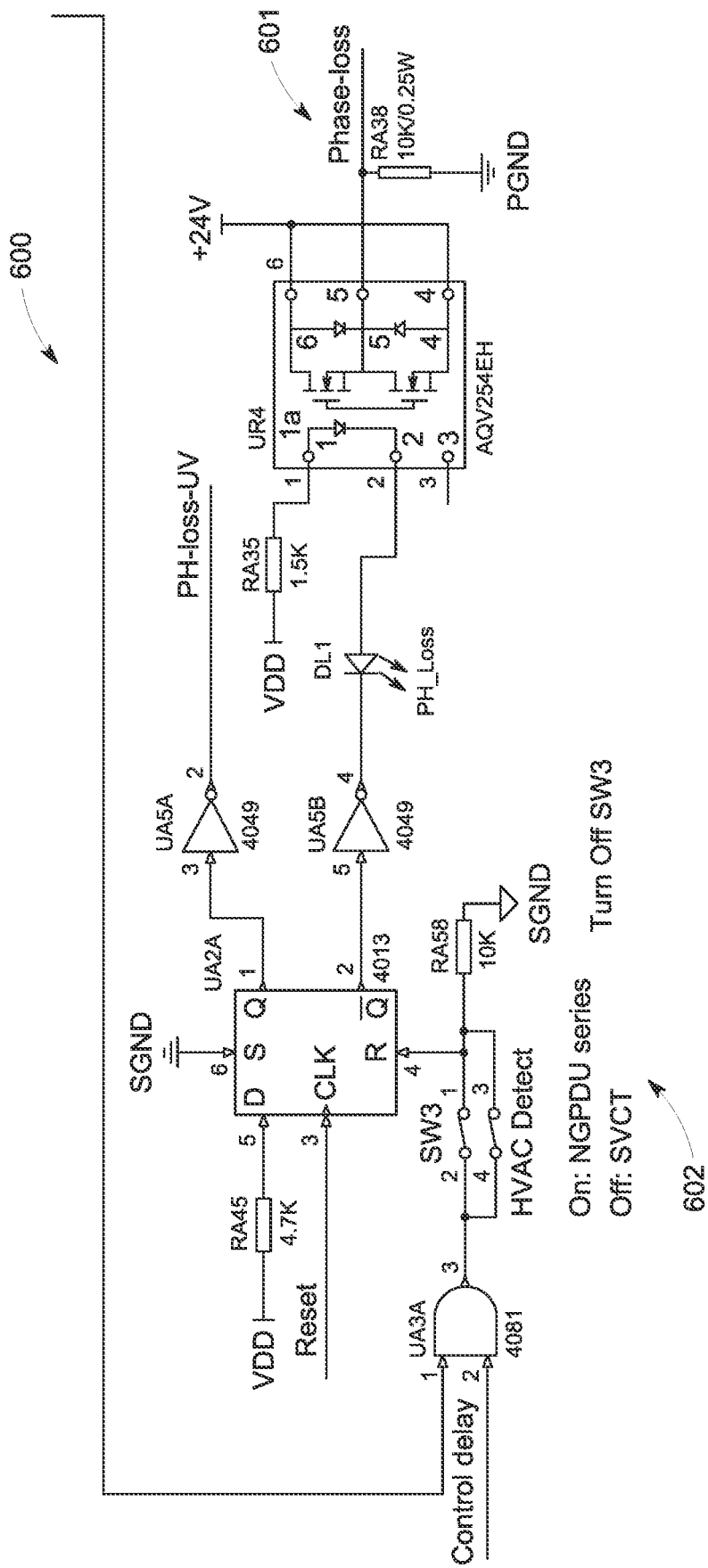
FIG. 6 shows a control board of the PDU.
Figure 7:
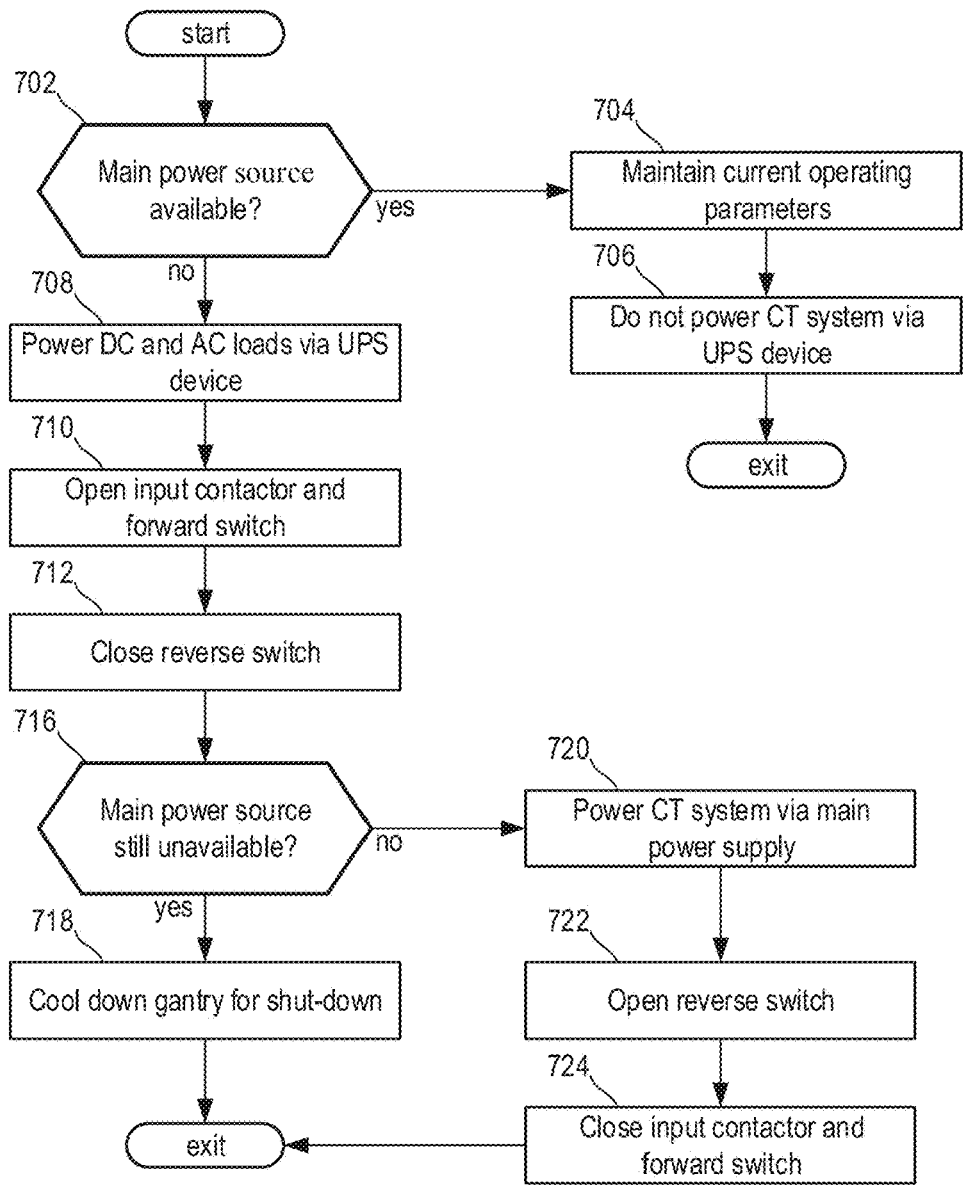
FIG. 7 shows a method for switching a power supply to the imaging system in response to an availability of power from the main power supply.
Figure 8:
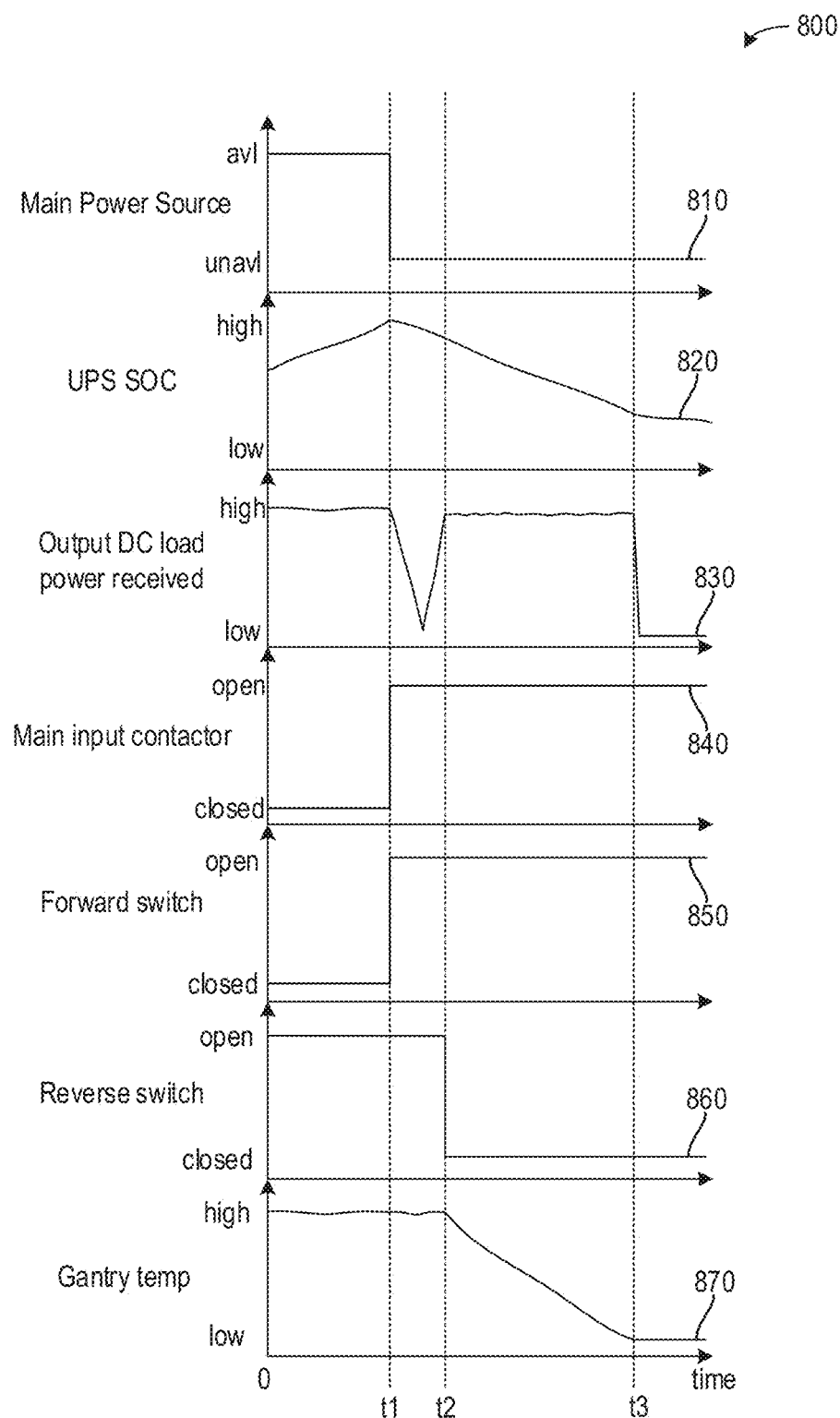
FIG. 8 shows a graphical example of the method of FIG. 7.

The following description relates to embodiments of a back-up power system for an imaging system, as illustrated in FIGS. 1 and 2. The back-up power system for the imaging system may be configured as an uninterruptible power supply (UPS) coupled to a power distribution unit (PDU) of the imaging system, as shown in FIGS. 3 and 4. A control circuit of a hot landing switch of the UPS is shown in FIG. 5. A control board of the PDU is shown in FIG. 6. A method for operating the UPS based on an availability of power from a main power supply is shown in FIG. 7. A graphical example of the method of FIG. 7 is illustrated in FIG. 8.

In one example of the present disclosure, the imaging system may include a gantry. The gantry may include a bearing, such as a liquid bearing, which may be cooled following operation. To execute a cooling routine of the bearing of the gantry, power, such as electrical energy, may be consumed. In an event where power is not supplied to the imaging system, shutdown of the gantry may occur without cooling the bearing, which may result in degradation and/or a reduced useful life.

In many applications, the imaging system may be arranged proximate to a UPS system configured to provide back-up power to a computer and a console of the imaging system. However, the UPS system is not wired to provide power to the gantry to enable a desired cooling prior to shut down in the event where a main power source is interrupted (e.g., absent). Furthermore, the gantry may not be sized to power the computer, the console, and the gantry for an extended period of time.

The inventors have recognized these drawbacks and come up with ways to adjust one or more electrical circuits between the UPS and the PDU to supply power from the UPS to the gantry when the main power source is unavailable. By doing this, an extra power source apart from the pre-existing UPS is not needed, which may decrease manufacturing and installation costs while also decreasing a packaging size of the system. For example, by adding multiple contactors (e.g., switches), a source of the power supply may be reliably controller such that both supplies are not providing power simultaneously.

FIGS. 1 to 6 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

Though a CT imaging system is described by way of example, it should be understood that the present methods and systems may also be useful when applied to other imaging systems, such as x-ray imaging systems, magnetic resonance imaging (MRI) systems, positron emission tomography (PET) imaging systems, single-photon emission computed tomography (SPECT) imaging systems, ultrasound imaging systems, and combinations thereof (e.g., multi-modality imaging systems, such as PET/CT, PET/MR or SPECT/CT imaging systems). The present discussion of a CT imaging system is provided merely as an example of one suitable imaging system.

FIG. 1 illustrates an exemplary CT imaging system 100 configured for CT imaging. Particularly, the CT imaging system 100 is configured to image a subject such as a patient, an inanimate object, one or more manufactured parts, and/or foreign objects such as dental implants, stents, and/or contrast agents present within the body. In one embodiment, the CT imaging system 100 includes a gantry 102, which in turn, may further include at least one x-ray source 104 configured to project a beam of x-ray radiation 106 (see FIG. 2). Specifically, the x-ray source 104 is configured to project the x-ray radiation beams 106 towards an x-ray detector array 108 positioned on the opposite side of the gantry 102. Although FIG. 1 depicts only a single x-ray source 104, in certain embodiments, multiple x-ray sources and detectors may be employed to project a plurality of x-ray radiation beams 106 for acquiring projection data at different energy levels corresponding to the patient. In some embodiments, the x-ray source 104 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT imaging system 100 further includes an image processor 110 configured to reconstruct images of a target volume of the subject using an iterative or analytic image reconstruction method. For example, the image processor 110 may use an analytic image reconstruction approach such as filtered back projection (FBP) to reconstruct images of a target volume of the patient. As another example, the image processor 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject. As described further herein, in some examples the image processor 110 may use both an analytic image reconstruction approach such as FBP in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of detector elements. The intensity of the attenuated x-ray radiation beam received at the detector array is dependent upon the attenuation of an x-ray radiation beam by the object. Each detector element of the array produces a separate electrical signal that is a measurement of the x-ray beam attenuation at the detector location. The attenuation measurements from all the detector elements are acquired separately to produce a transmission profile.

In some CT imaging systems, the x-ray source and the detector array are rotated with a gantry within the imaging plane and around the object to be imaged such that an angle at which the x-ray radiation beam intersects the object constantly changes. A group of x-ray radiation attenuation measurements, e.g., projection data, from the detector array at one gantry angle is referred to as a "view." A "scan" of the object includes a set of views made at different gantry angles, or view angles, during one revolution of the x-ray source and detector.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

The CT imaging system 100 may receive power from a main power source 122 or from an uninterruptible power source (UPS) 124 through a power distribution unit (PDU) 120. Additionally or alternatively, the CT imaging system may receive power from a generator, wherein power from the generator may be provided through a similar coupling as the main power source 122. In one example, the PDU 120 may include one or more sensors configured to sense an availability of power from the main power source 122. A PDU controller 130 may be configured to receive feedback from the plurality of sensors and adjust a position of one or more actuators in response to the availability of power from the main power source 122. In one example, the one or more actuators are contactors and/or switches, configured to alternate between the main power source 122 and the UPS 124 based on the availability of power from the main power source 122. In one example, if power from the main power source is unavailable, then the PDU controller 130 may signal to actuate a first switch to break a circuit in which the main power source 122 is arranged and to actuate a second switch to complete a circuit in which the UPS 124 is arranged such that power is supplied from the UPS 124 to the CT imaging system, as will be described in greater detail below.

The PDU controller 130 may include instructions stored on memory thereof that when executed cause the PDU controller 130 to adjust switches controlling power received from the main power source 122 when power from the main power source is unavailable. Power from the main power source 122 may be detected via a current sensor (illustrated in FIG. 6). Feedback from the current sensor may prompt the PDU controller 130 to actuate switches from the main power source 122 while actuating a UPS switch from the UPS to output loads of the PDU 120 to power the CT imaging system 100.

FIG. 2 illustrates an exemplary imaging system 200 similar to the CT imaging system 100 of FIG. 1. In accordance with aspects of the present disclosure, the imaging system 200 is configured for imaging a subject 204. In one embodiment, the imaging system 200 includes the detector array 108 (see FIG. 1). The detector array 108 further includes a plurality of detector elements 202 that together sense the x-ray radiation beam 106 (see FIG. 2) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macro-detectors, as described further herein. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

In one embodiment, the display 232 allows the operator to evaluate the imaged anatomy. The display 232 may also allow the operator to select a volume of interest (VOI) and/or request patient information, for example, via a graphical user interface (GUI) for a subsequent scan or processing.

In one example, the UPS 124 of FIG. 1 may be a preexisting UPS of the computing device 216 and auxiliary components thereof (e.g., the display 232, the operator console 220, etc.). As will be described herein, the inventors have found a way to modify one or more circuits of the PDU 120 and the UPS 124 of FIG. 1 such that the UPS 124 previously configured to only power the computing device 216 when the power from the main power supply 122 was unavailable to also power the gantry 102. As such, a desired cooling of the gantry 102 may be executed in response to an event where power from the main power supply 122 is unavailable.

Turning now to FIG. 3, it shows an embodiment 300 of a power interface of the UPS device 124 and the main power source 122 with the PDU 120. As such, components previously introduced may be similarly numbered in this figure and subsequent figures.

The main power source 122 may include a circuit along which a breaker 302, a main power input contactor 304, and a primary transformer 306. The main power source 122 may include a plurality of electric lines 308, arranged in parallel and extending through corresponding switches in the main power input contactor 304 to the primary transformer 306. The breaker 302 may be configured to trip in response to 150 A (amps) or more of current flowing through any of the plurality of electric lines 308.

The primary transformer 306, which includes an electric winding configured to draw power from the plurality of electrical lines or wires 308. The winding may be electrically coupled to windings of a first secondary transformer 310 and a second secondary transformer 330. The main power input contactor 304 may be adjusted via a signal sent to an actuator thereof via a PDU controller (e.g., PDU controller 130 of FIG. 1) in response to power from the main power source 122 being absent. The main power input contactor 304 may be actuated to an open or a closed position, wherein the closed position completes the circuit and allows current to flow from the main power source 122 to the primary transformer 306.

The first secondary transformer 310, which may include a higher voltage than the second secondary transformer 330, may direct power, via a plurality of electric wires 312, to a rectifier 315. The plurality of electrical lines or wires 312 may each include contactors 314 configured to disrupt the circuit in response to a current flow through the plurality of electrical lines or wires exceeding a rating of the contactors 314. The rectifier 315 may be a passive or active rectifier, configured to convert alternating current (AC) to direct current (DC). The DC lines or wires are coupled to an output DC load 320, which may be used to supply power to a gantry (e.g., gantry 108 of FIG. 1). In one example, electrical power supplied to the output DC load 320 is a relatively high voltage (e.g., greater than 600V DC).

The second secondary transformer 330, which may direct power, via a plurality of electrical lines or wires 332, to an output AC load 340. Each of the plurality of electrical lines or wires 332 may include a contactor, of a plurality of contactors 334, rated to disrupt the circuit in response to an electrical current exceeding a rating of the contactor. In one example, the contactors are rated to 50A. However, the contactors may be rated to other amperages based on a sizing and amp rating of the plurality of electric wires 332. The output AC load 340 may send power to lower power demand devices, such as a console, power cabinet, computer, and the like.

The plurality of electrical lines or wires 332 may include a first splice 350 and a second splice 360. A plurality of first UPS electrical lines or wires 352 may be electrically coupled to the plurality of electrical lines or wires 332 at the first splice 350. A plurality of second UPS electrical lines or wires 362 may be electrically coupled to the plurality of electrical lines or wires 332 at the second splice 360. Each of the plurality of first and second UPS electrical lines or wires 352, 362 may be coupled to an interlocking switch 354. The interlocking switch 354 may be configured to adjust a position of a power-to position 356 and a power-from position 358 in tandem. Operation of the interlocking switch 354 in combination with the main power input contactor 304 is described in greater detail below.

The plurality of first and second UPS electrical lines or wires 352, 362 may be electrically coupled to a terminal block 364 and to input and output terminals of the UPS 124.

During operating conditions where the main power source 122 is active and providing power to the circuit, the main power input contactor 304 may be in a closed position. Power from the main power source 122 may be coupled to each of the output DC load 320, output AC load 340, and input of the UPS 124. Thus, the gantry and the console may be powered by the main power source 122. Furthermore, a state-of-charge (SOC) of the UPS 124 may be replenished. As such, the power-to position 356 of the interlocking switch 354 may be in a closed position. The power-from position 358, which corresponds to a position of the interlocking switch 354 configured to allow the UPS 124 to directly power the output DC load 320 and the output AC load 340 is in an open position (as illustrated). Thus, power to the output AC load 340 is coupled through the plurality of electrical lines or wires 332, through the plurality of first UPS electrical lines or wires 352, through the UPS 124, through the plurality of second UPS electrical lines or wires 362, back to the plurality of electrical lines or wires 332, and to the output AC load 340. By opening the power from position 358, power from the UPS 124 may be blocked from the grid (e.g., the main power source 122). Herein, the power-to position 356 and the power-from position 358 may be interchangeably referred to as the power-to switch 356 and the power-from switch 358, respectively.

If power from the main power source 122 is interrupted and/or unavailable, then the main input contactor 304 and the power-to position 356 of the interlocking switch 354 are switched to open positions, via signals from the PDU controller to corresponding actuators and the power-from position 358 of the interlocking switch 354 is switched to a closed position. In one example, the interlocking switch 354, which may be mechanically or electronically controlled, may block the power-to and power-from positions to be open or closed simultaneously, thereby protecting circuits of the PDU 120. As such, the power-to switch and the power-from switch may be interlocked with one another. Thus, power from the UPS 124 may be coupled to the output AC load 340, as described above, and to the output DC load 320. Power from the UPS 124 may be coupled through the plurality of second UPS electrical lines or wires 362, through the closed power from switch 358, through the plurality of electrical lines or wires 332, and to the second secondary transformer 330. The second secondary transformer 330 may direct the power to the primary transformer 306, which then increases a voltage of the power and directs it to the first secondary transformer 310. The power from the first secondary transformer 310 is converted from AC to DC at the rectifier 315, and then directed to the output DC load 320. By doing this, a preexisting UPS (e.g., UPS 124), originally sized to only power the output AC load 340 in response to the main power source 122 being unavailable, may be used to power the output DC load 320.

Turning now to FIG. 4, it shows an embodiment 400 illustrating an example of modifications to a previous example of circuitry of the PDU 120, the main power source 122, and the UPS 124 to modify electrical output of the UPS 124 to provide power to the gantry 108 when power from the main power source 122 is unavailable. As mentioned above, the UPS 124 may be a 120V UPS originally sized to power only the console and the computer in response to the main power source 122 being unavailable. However, via inclusion of the contactors, multi-phase diodes.

In one example, the PDU 120 may include a first terminal strip 410, including a plurality of jumpers 420 extending therefrom. The plurality of jumpers 420 may be disconnected in order to electrically couple the UPS 124 to the PDU 120. Input power from the PDU to the UPS is connected at terminal strip 410 sites 1, 2, and 3. Output power from the UPS to the PDU is connected at terminal strip 410 sites 6, 7, and 8. Electrical wires, which may be triplex wires, may include where the neutral and ground may be connected to a second terminal strip 420. The UPS 124 is illustrated as a three-phase UPS in the example of FIG. 4. In some examples, the UPS 124 may be a two-phase UPS, wherein the UPS may connect to only four sites of the terminal strip 410.

Turning now to FIG. 5, it shows an embodiment of a control circuit 500 of the UPS (e.g., UPS 124 of FIGS. 1, 3, and 4). FIG. 6 shows an embodiment of a control circuit 600 of the PDU (e.g., PDU 120 of FIGS. 1, 3, and 4).

FIG. 5 shows the control circuit schematic 500 of the main circuit 300 which included main contactor 304, forward 356, reverse 358 and KXG 314 contactors. Power-to position and power-from position are interchangeably referred to as forward contactor 356 and reverse contactor 358 herein. The coil 502 of main contactor 304 is energized from main input power 308. The input power voltage 308 is 480V as an example. Two 2 A fuses 501 are positioned to protect the coil 502 for short circuit or over current. The coil 502 has electrical interlock with reverse contactor 358 by using two contacts NC REV 505, which are closed when the utility power source is available, to ensure that the reverse contactor 358 is not energized and there is no power from the UPS 124 to the second secondary winding 330.

The control circuit 500 includes two 120V input power source such as a first source 510 and a second source 511. The first source 510 is coupled to circuit breaker CB9 440 of FIG. 4 which is connected to phase A of UPS 124. The second source 511 is coupled to circuit breaker CB3 430 which is connected to the phase A of the second secondary winding 330. It is possible to have both 120V power sources 510 and 511 providing power when the utility power source is available. The control circuit 500 may have only 120V power from the first source 510 from UPS 124 during a power outage condition when the utility power source is unavailable. In another example, the control circuit 500 may have only 120 power from the second source 511 from secondary winding 330 because the customer may not use UPS 124 for service or maintenance. Therefore, a three phase diode bridge 506 is used to allow the control circuit 500 to receive power at all three conditions.

The coil 503 of FWD contactor 356 can be energized when the auxiliary contact 520 of the main contactor 304 is closed and also the REV contactor 358 is opened by closing the normally close contact 523 of the REV contactor 358 in response to the utility power source being unavailable. If the FWD contactor 356 is closed, then the power from the secondary of transformer 330 is coupled to the UPS 124 to charge the UPS batteries. This is a condition on the CT imaging system 100 where the utility power source is available. The coil 504 of REV contactor 358 can be energized when the normally open (e.g., when the utility power source is available) of the auxiliary contact 521 of the KXG contactor 314 is closed and the FWD contactor 356 is opened by closing the normally close contact 522 of the FWD contactor 356. If the REV contactor 358 is closed, then the power from the UPS 124 goes to the second secondary winding of transformer 330 and then transfer to the first secondary winding 310 and after rectifying by 315, the HVDC power will be available on output terminals 320. This may be a power outage case of CT imaging system 100. During a power outage where the utility power source is unavailable to the CT imaging system 100, there is an interlock circuit 530 between hardware and software CT imaging system 100 to protect the UPS 124 from an overcurrent or overload condition. The external interlock circuit 530 is in series with normally closed contact 532 of the REV contactor 358. If the contact 532 is opened then the CT imaging system is under power outage condition and the external interlock circuit 530 is opened. The missing signal of the external interlock circuit 530 goes to image processor 110 and then the CT imaging system 102 cannot scan. Therefore, the UPS 124 will be protected for overload condition.

FIG. 6 illustrates an embodiment 600 of a part of a control board of PDU 120. The control board is configured to check the low voltage AC power of the second secondary winding of PDU 120 by two Voltage Monitoring Relay (VMR-1) 450 and (VMR-2) 460. If there is a phase loss or three phase voltages are not balanced, then the phase-loss signal 601 of circuit 600 will not allow KXG contactor 314 to close and the HVDC power will not be available on the output HVDC terminals 320. To avoid this condition during power outage, or during transferring power delivery from main power 122 to UPS 124, the SW3 602 will be turned off.

Turning now to FIG. 7, it shows a method 700 for adjusting an energy source based on an availability of electrical energy from a main power source. Instructions for the method may be executed by and stored on memory of a controller of the PDU (e.g., PDU controller 130 of FIG. 1). The controller may be configured to receive inputs from one or more sensors of the PDU and adjust operation of one or more switches to change the direction of current flow.

The method 700 begins at 702, which includes determining if a main power source is available. In one example, a voltage of the main power source may be sensed by a voltage sensor including a circuit, as shown in FIG. 6. If the main power source is unavailable, then the voltage sensor may detect a voltage less than a threshold voltage. In one example, the threshold voltage is a non-zero, positive number. The threshold voltage may be 110 VAC or more.

If the main power source is available, then the method 700 may proceed to 704, which includes maintaining current operating parameters. In one example, current operating parameters may include where current flows from the main power source to the output DC load and from the main power source to the UPS. Current from the UPS may be coupled to the output AC load. As such, a main contactor (e.g., main power input contactor 304 of FIG. 3) and a forward switch (e.g., power to switch 356 of FIG. 3) may be closed and a reverse switch (e.g., power from switch 358 of FIG. 3) may be open.

The method 700 may proceed to 706, which includes where the CT imaging system is not powered via the UPS device. As such, the gantry and other components of the CT imaging system powered by the output DC load may receive power from the main power source and operate without entering a cooling shut-down mode.

Returning to 702, if the main power source is unavailable, then the method 700 may proceed to 708, which includes powering DC and AC loads via the UPS device.

The method 700 may proceed to 710, which includes opening the input contactor and the forward switch. As such, the circuit between the main power source and a primary transformer may be disconnected.

The method 700 may proceed to 712, which includes closing the reverse switch. As such, the UPS may be electrically coupled to a second secondary transformer. Current from the UPS maybe coupled to each of the output AC load and the second secondary transformer when the main power source is interrupted (e.g., unavailable). The second secondary transformer may direct the current to the primary transformer, and then to the rectifier, where the AC current is converted to DC and then directed to the output DC load.

The method 700 may proceed to 716, which includes determining if the main power source is still unavailable. If the main power source is still unavailable, then the method 700 may proceed to 718 which includes cooling down the gantry for shut-down. Cooling down the gantry for shut-down may include powering the gantry via the UPS as a cooling system of the gantry is adjusted to a threshold cooling setting. The threshold cooling setting may correspond to a maximum cooling setting wherein a heat exchanger pump is adjusted to a high speed, a heat exchanger fan is adjusted to a high speed, a detector thermal system is adjusted to a high speed, cooling fans are adjusted to a high speed, and a gantry rotation is adjusted to between 0 sec/rev to 0.28 sec/rev. By doing this, the gantry may quickly cool down via power from the UPS.

In some examples, the method 700 may proceed to 718 without waiting for the threshold duration to elapse. For example, if a SOC of the UPS is less than a threshold SOC, then the gantry may enter the shut-down mode. In one example, the SOC of the UPS may be tracked via monitoring power consumed from the UPS and power supplied to the UPS.

If the main power source is now available, or if power from the back-up generator is available, then the method 700 may proceed to 720, which includes powering the CT imaging system via the main power source or the back-up generator. Thus, the UPS device may no longer supply power to the output DC load.

The method 700 may proceed to 722, which includes opening the reverse switch.

The method 700 may proceed to 724, which includes closing the input contactor and forward switch immediately. As such, power may again be coupled from the main power source, through the main input contactor, through the primary transformer, through the secondary transformer, through the forward switch, to the UPS, and to the output AC load. The current flow to the UPS may recharge a SOC of the UPS. Additionally, power from the main power source may be coupled through the closed main input contactor, through the primary transformer, through the first secondary transformer, through the rectifier, and to the output DC load.

In some examples, additionally or alternatively, a CT imaging system monitor may provide an error alert in response to the UPS providing power to the system may include reporting a fault condition of the UPS. In one example, this may be due to batteries of the UPS. In one example, by replacing the batteries of the UPS, the alert may no longer be displayed in response to the UPS powering the CT imaging system. Additionally or alternatively, during a first instance of the error alert, the error alert may be accompanied by an instruction to change batteries of the UPS to enhance back-up power provided by the UPS during future power outages.

Turning now to FIG. 8, it shows a graph 800 illustrating adjustments to the PDU to maintain power to the gantry during a power outage. Plot 810 illustrates an availability of a main power source. Plot 820 illustrates a UPS SOC. Plot 830 illustrates power received by the output DC load. Plot 840 illustrates a position of a main input contactor. Plot 850 illustrates a position of a forward switch. Plot 860 illustrates a position of a reverse switch. Plot 870 illustrates a gantry temperature. Time increases from a left to a right side of the figure.

Prior to t0, the main power source (plot 810) is available. As such, the UPS SOC increases (plot 820) as current flows through the closed main input contactor (plot 840) and the closed forward switch (plot 850) to the UPS. The output DC load receives a relatively high amount of power from the main power source (plot 830). The reverse switch is in an open position (plot 860) to block current from flowing from the UPS to the main power source. The gantry temperature is relatively high (plot 870) due to the CT imaging system being used (e.g., scanning a patient).

At t1, the main power source is unavailable. As such, the UPS SOC stops being replenished. The main input contactor and the forward switch are moved to open positions. Between t1 and t2, the UPS SOC begins to decrease as power is transferred from the UPS to the output AC load and the output DC load. As illustrated, the power received by the output DC load may decrease to a relatively low amount prior to returning to a relatively high amount. The drop in power may correspond to a gap between the main power source becoming unavailable and the UPS being activated and powering the output DC load. In some example, the gap in power provided may be avoided. The gantry temperature remains relatively high as the gantry operation is uninterrupted or unchanged prior to t2.

At t2, a transferring time has passed and the main power source is still unavailable. The reverse switch is moved to a closed position. As such, the gantry temperature may begin to decrease as a gantry controller may signal a cool-down prior to a shut-down of the gantry. Additionally or alternatively, when the main power source is unavailable, the gantry may be switched to the cooling/shut-down mode if the UPS SOC is less than a threshold SOC, wherein the threshold SOC is based on a minimum SOC needed to cool the gantry prior to shut-down. The threshold SOC may be further based on the UPS powering the console so that a user may save their work. Between t2 and t3, the gantry cooling is executed via power from only the UPS. The gantry temperature decreases to a relatively low temperature so that the gantry may be shut-down due to the absence of power from the main power source. At t3, the gantry temperature is relatively low and it is shut-down. After t3, a rate at which the UPS SOC is consumed is reduced since the UPS may power only the output AC loads with lower power demands.

An embodiment of a system, comprises a power distribution unit configured to receive power from a main power source and an uninterruptible power supply (UPS), wherein the UPS is configured to directly power an output AC load, the UPS is further configured to power an output DC load after coupled through one or more transformers. In one embodiment the system further includes where the UPS is configured to power the output DC load via passing current through a primary transformer, a first secondary transformer, and a second secondary transformer. In one embodiment, the system further includes where an interlock switch is moved to a position to couple the UPS, to the second secondary transformer, to the primary transformer, to the first secondary transformer, to a rectifier, and to the output DC load. In one embodiment, the system further includes where a main input contactor is in an open position to block current from the primary transformer to the main power source. In one embodiment, the system further includes where the output AC load supplies power to a console and a computer. In one embodiment, the system further includes where the output DC load supplies power to a gantry of a computer tomography system. In one embodiment, the system further includes where the UPS is configured to power the output AC load and the output DC load in response to power from the main power source being unavailable.

An example of a medical imaging system, comprises a gantry coupled to an output DC load, a power cabinet coupled to an output AC load, a power distribution unit (PDU) comprising a primary transformer, a first secondary transformer, and a second secondary transformer, wherein the power distribution unit is configured to receive power from one of a main power source and an uninterruptible power supply (UPS), and a controller with computer readable instructions stored on memory thereof that cause the controller to adjust a position of an input power switch and a forward switch to an open position in response to power from the main power source being unavailable, and adjust a position of a reverse switch to couple power form the UPS to the output AC load and the output DC load. In one embodiment, the medical imaging system further includes where the gantry enters a shut-down mode in response to a threshold duration elapsing following the reverse switch being adjusted to the closed position. In one embodiment, the medical imaging system further includes where the gantry enters a shut-down mode in response to a state-of-charge (SOC) of the UPS being less than a threshold SOC, wherein the threshold SOC is based on an amount of power used to cool the gantry during the shut-down mode. In one example, the medical imaging system further includes where power is coupled directly from the UPS to the output AC load when the reverse switch is closed. In one example, the medical imaging system further includes where power is coupled to the output DC load when the main power source is unavailable includes power from the UPS, through the closed reverse switch, to the second secondary transformer, through the primary transformer, through a first secondary transformer, through a rectifier, and to the output DC load. In one example, the medical imaging system further includes where a voltage of the first secondary transformer is greater than a voltage of the second secondary transformer. In one example, the medical imaging system further includes where the instructions further enable the controller to adjust the position of the reverse switch to an open position and the positions of the input power switch and the forward switch to a closed position in response to power from the main power source being available. In one example, the medical imaging system further includes where the forward switch and the reverse switch are arranged on an interlock switch.

An embodiment of a method for a computer-tomography (CT) system, the method executed via instructions stored on memory of a controller, the method, comprising in response to a main power source being unavailable, powering an output AC load directly via an uninterruptible power supply (UPS) and powering an output DC load via power coupled from the UPS to a second secondary transformer, to a primary transformer, to a first secondary transformer, and through a rectifier. In one embodiment, the method further includes adjusting a position of an input power contactor to an open position to disconnect the primary transformer from the main power source. In one embodiment, the method further includes adjusting a position of a reverse switch to a closed position to couple the UPS to the second secondary transformer and a position of a forward switch to an open position to block current from returning to the UPS. In one embodiment, the method further includes powering a console via the output AC load and a gantry of the CT imaging system via the output DC load. In one embodiment, the method further includes cooling the gantry in response to the UPS powering the output DC load for longer than a threshold duration or a state-of-charge (SOC) of the UPS being less than a threshold SOC.

As used herein, an element or step recited in the singular and proceeded with the word "a" or "an" should be understood as not excluding plural of said elements or steps, unless such exclusion is explicitly stated. Furthermore, references to "one embodiment" of the invention do not exclude the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A system, comprising:
   a power distribution unit configured to receive power from a main power source and an uninterruptible power supply (UPS), wherein the UPS is configured to directly power an output AC load, the UPS is further configured to power an output DC load after coupled through one or more transformers, wherein the UPS is configured to power the output DC load via passing current through a primary transformer, a first secondary transformer, and a second secondary transformer;
   a main input contactor coupled between the main power source and the primary transformer and configured to be in an open position to block current between the primary transformer and the main power source responsive to power from the main power source being interrupted and/or unavailable; and
   an interlock switch coupled between the second secondary transformer and the UPS, the interlock switch having a power-to switch and a power-from switch, wherein the power-to switch is configured to be in an open position to block current between the second secondary transformer and the UPS responsive to power from the main power source being interrupted and/or unavailable.

2. The system of claim 1, wherein the output AC load supplies power to a console and a computer.

3. The system of claim 1, wherein the output DC load supplies power to a gantry of a computer tomography system.

4. The system of claim 1, wherein the UPS is configured to power the output AC load and the output DC load in response to power from the main power source being interrupted and/or unavailable.

5. A medical imaging system, comprising:
   a gantry coupled to an output DC load;
   a power cabinet coupled to an output AC load;
   a power distribution unit (PDU) comprising a primary transformer, a first secondary transformer, and a second secondary transformer;
   wherein the power distribution unit is configured to receive power from one of a main power source and an uninterruptible power supply (UPS);

a main input contactor coupled between the main power source and the primary transformer;

an interlock switch coupled between the second secondary transformer and the UPS, the interlock switch having a power-to switch and a power-from switch; and a controller with computer readable instructions stored on memory thereof that cause the controller to:

adjust a position of the main input contactor and the power-to switch to an open position in response to power from the main power source being interrupted and/or unavailable; and adjust a position of the power-from switch to a closed position to couple power from the UPS to the output AC load and the output DC load.

6. The medical imaging system of claim 5, wherein the gantry enters a shut-down mode following the power-from switch being adjusted to the closed position.

7. The medical imaging system of claim 5, wherein the gantry enters a shut-down mode in response to a state-of-charge (SOC) of the UPS being less than a threshold SOC, wherein the threshold SOC is based on an amount of power used to cool the gantry during the shut-down mode.

8. The medical imaging system of claim 5, wherein power is coupled directly from the UPS to the output AC load when the power-from switch is closed.

9. The medical imaging system of claim 5, wherein power is coupled to the output DC load when the main power source is unavailable includes power from the UPS, through the closed power-from switch, to the second secondary transformer, through the primary transformer, through a first secondary transformer, through a rectifier, and to the output DC load.

10. The medical imaging system of claim 9, wherein a voltage of the first secondary transformer is greater than a voltage of the second secondary transformer.

11. The medical imaging system of claim 5, wherein the instructions further enable the controller to adjust the position of the power-from switch to an open position and the positions of the main input contactor and the power-to switch to a closed position in response to power from the main power source being available.

* * * * *